United States Patent
Gonda (12)

(10) Patent No.: US 6,227,195 B1
(45) Date of Patent: *May 8, 2001

(54) COARSE SPRAY DELIVERY OF FUNCTIONAL BIOLOGIC MATERIAL

(75) Inventor: Igor Gonda, San Francisco, CA (US)

(73) Assignee: Genentech, Inc., San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/797,686

(22) Filed: Feb. 3, 1997

Related U.S. Application Data

(63) Continuation of application No. 08/439,977, filed on May 22, 1995, now abandoned.

(51) Int. Cl.$^7$ .................... A61M 15/00; A61M 16/00; A62B 18/00; A62B 7/00; A62B 9/00
(52) U.S. Cl. ...................... 128/200.24; 128/898
(58) Field of Search .................. 128/200.14, 200.15, 128/200.16, 200.17, 200.18, 200.19, 200.21, 200.22, 200.23, 203.12, 206.16, 204.14, 200.24, 898

(56) References Cited

U.S. PATENT DOCUMENTS

| | | | |
|---|---|---|---|
| 4,590,206 | * | 5/1986 | Forrester et al. .................... 514/456 |
| 4,895,719 | * | 1/1990 | Radhakishan et al. ................ 424/45 |
| 4,906,476 | * | 3/1990 | Radhakishan ........................ 424/450 |
| 5,031,613 | * | 7/1991 | Smith et al. .................... 128/203.12 |
| 5,058,577 | * | 10/1991 | Six .................................. 128/207.14 |
| 5,173,298 | * | 12/1992 | Meadows ............................. 424/427 |
| 5,313,939 | * | 5/1994 | Gonzalez ........................ 128/203.12 |
| 5,439,670 | * | 8/1995 | Purewal et al. ........................ 424/45 |
| 5,562,608 | * | 10/1996 | Sekins et al. .................. 128/207.15 |
| 5,579,758 | * | 12/1996 | Century ............................ 128/200.22 |
| 5,797,899 | * | 8/1998 | Tilton et al. ............................ 606/1 |
| 5,906,202 | * | 5/1999 | Schuster et al. ................ 128/203.23 |

OTHER PUBLICATIONS

Gonda, I., "Targeting by Deposition" *Pharmaceutical Inhalation Aerosol Technology* (Ed. A.J. Hickey), Marcel Dekker' Inc.: New York, 1992, pp. 61–82.

Ferron, G.A., et al., "Measurement of Mucociliary Clearance in the Upper Airways of Beagle Dogs." *J. Aerosol Sci.*, 22 (Suppl.1):S867–S870 (1991).

Kreyling, W.G., et al., "A Miniature Jet Nebulizer for Aerosol Bolus Delivery to Respiratory Airways Via Bronchoscopy," *J. Aerosol Sci.*, 24(Suppl.1):S451–S452 (1993).

Hoover, M.D., et al., "A Microspray Nozzle for Local Administration of Liquids or Suspensions to Lung Airways Via Bronchoscopy." *J. Aerosol Med.*, 6:67–72 (1993).

Gerrity, T.R., "Pathophysiological and Disease Constraints on Aerosol Delivery," *Respiratory Drug Delivery* (Ed. P.R. Byron) CRC PRess, Boca Raton, pp. 1–38 (1990).

Kim, C.S., et al., "Particle Deposition in Bifurcating Airway Models with Varying Airway Geometry." *J. Aerosol Sci.*, 25:567–581 (1994).

Cipolla, D., et al., "Characterization of Aerosols of Human Recombinant Deoxyribonuclease (rhDNase) Generated by Jet Nebulizers." *Pharm. Res.*, 11:491–497 (1994).

Cipolla, D.C., et al., "Assessment of Aerosol Delivery Systems for the Recombinant Human Deoxyribonuclease I (rhDNase)." *STP Pharm Sciences*, 4:50–62 (1994).

Sweeney, T.D., "Exposing Animals to Aerosols: Considerations that Influence Regional Lung Deposition." *J. Aerosol Med.*, 3:169–186 (1990).

Horsefield, K., et al., "Models of the Human Bronchial Tree." *J. Appl. Physiol.*, 31:207–217 (1971).

Schlesinger, R.B. et al., "Comparative Morphometry of the Upper Bronchial Tree in Six Mammalian Species." *Anat. Rec.*, 199:99–108 (1981).

Felicetti, S.A., et al., "Comparison of Tracheal Mucous Transport in Rats, Guinea Pigs, Rabbits, and Dogs." *J. Appl. Physiol.*, 51:1612–1617 (1981).

Bailey, M.R., et al., "An Interspecies Comparison of the Lung Clearance of Inhaled Monodisperse Cohalt Oxide Partiicles—Part I: Objectives and Summary of Results." *J. Aerosol Sci.*, 20(2):169–188 (1989).

\* cited by examiner

*Primary Examiner*—John G. Weiss
*Assistant Examiner*—Joseph F. Weiss, Jr.
(74) *Attorney, Agent, or Firm*—Flehr Hohbach Test Albritton & Herbert LLP

(57) ABSTRACT

The present invention relates to a method of introducing biologic materials into the conducting airways of the bronchial system. The invention involves the use of a liquid carrier or suspension for the biologic materials, delivered in relatively large droplet form at a velocity greater than the air velocity of the normally breathing subject. This method also can be used for localized delivery of such biologic materials, including diagnostic and imaging agents, into other gas-filled body cavities.

25 Claims, 6 Drawing Sheets

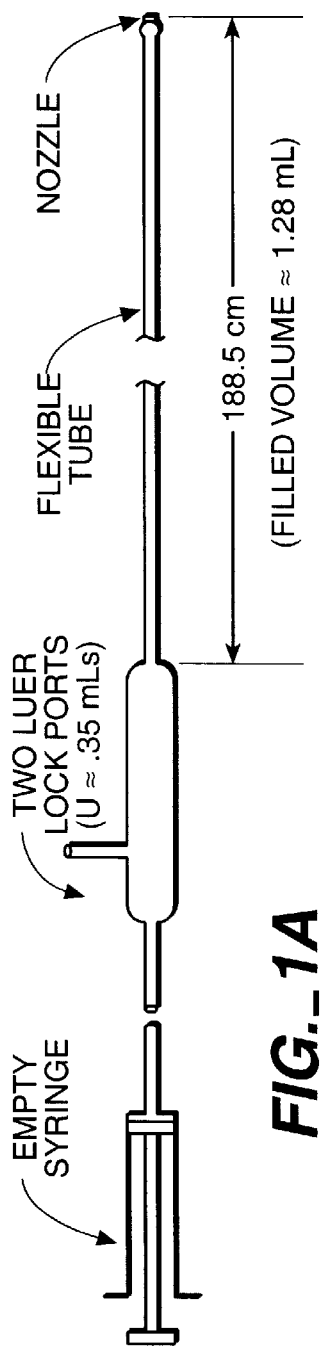
FIG._1A
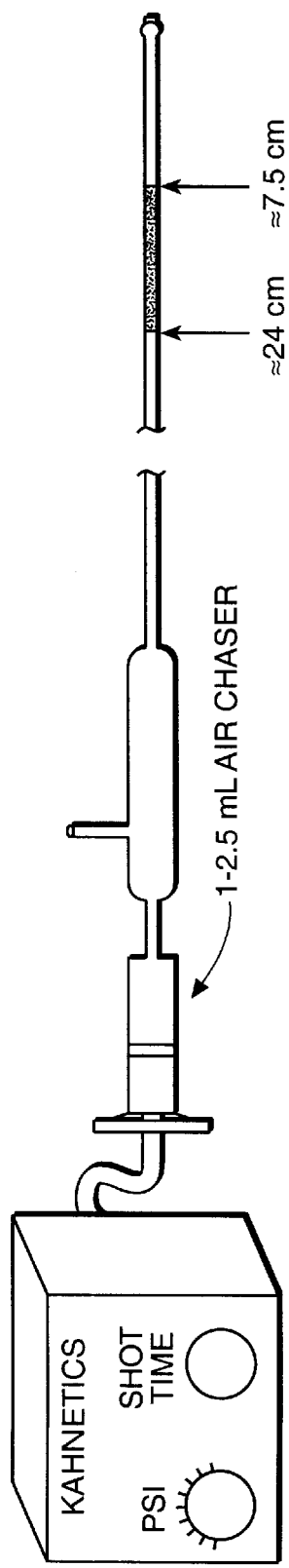
FIG._1B
FIG._1C

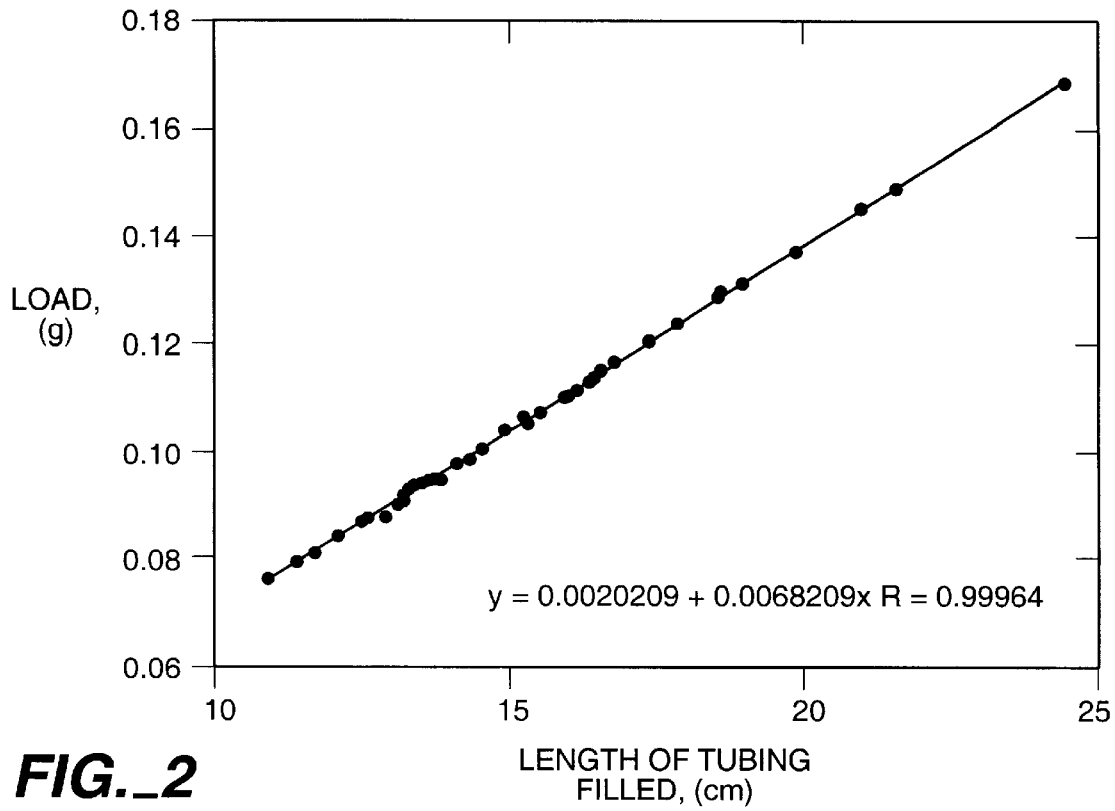
FIG._2
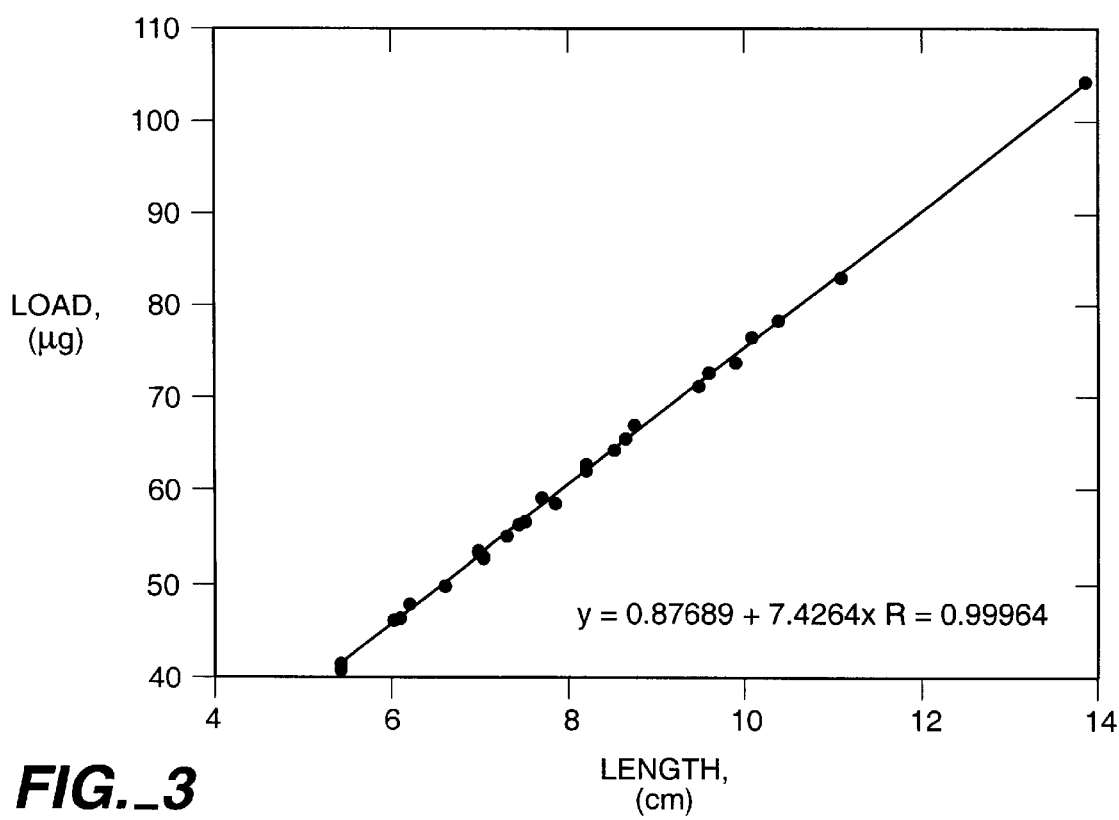
FIG._3

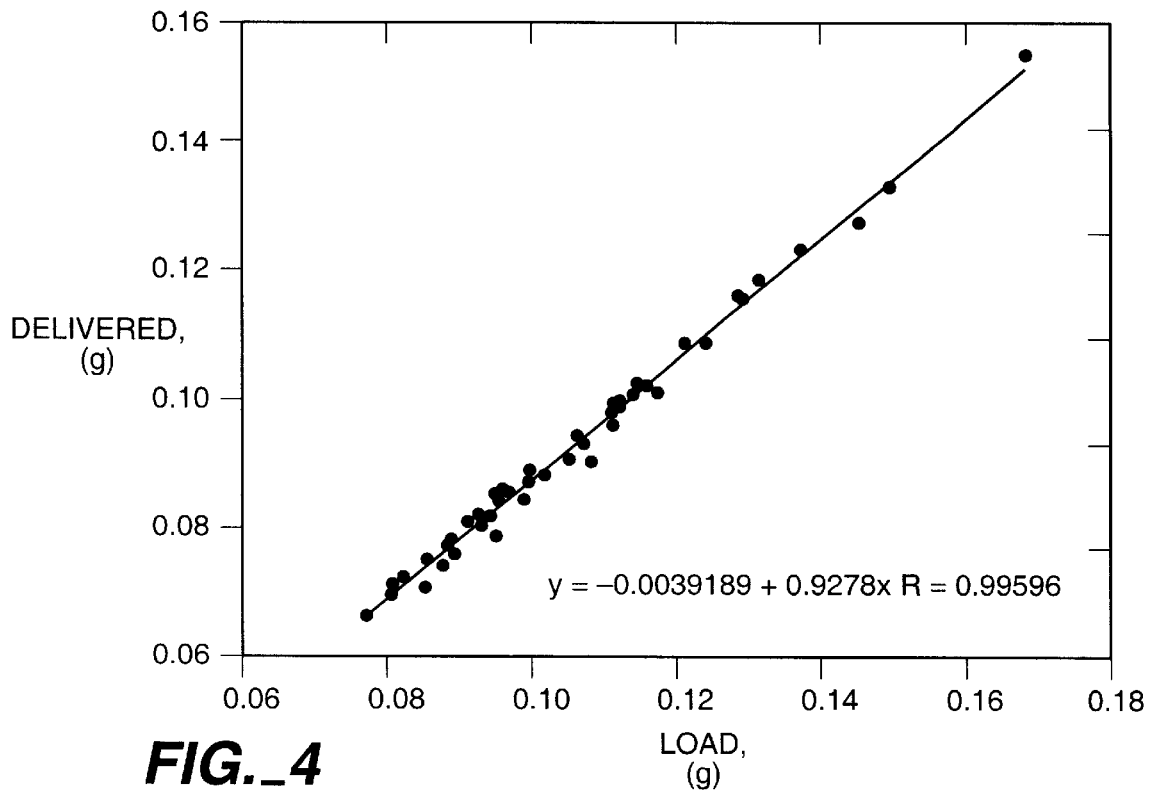
FIG._4
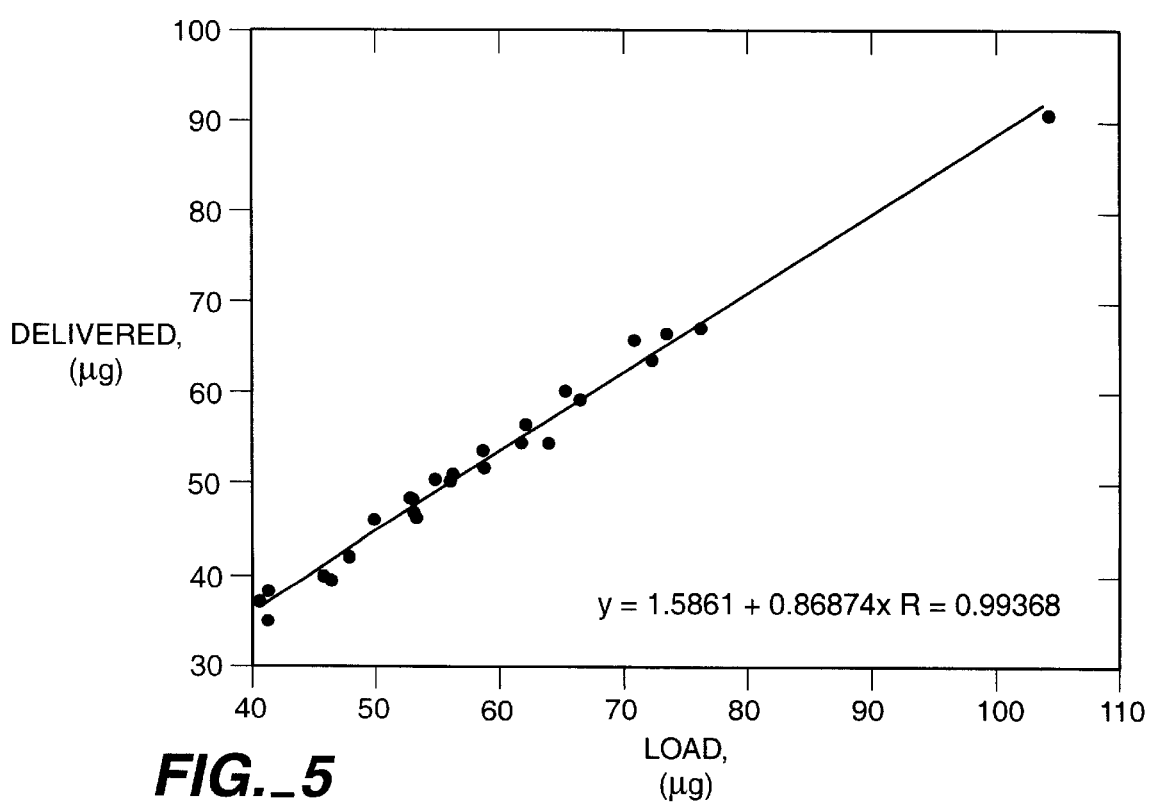
FIG._5

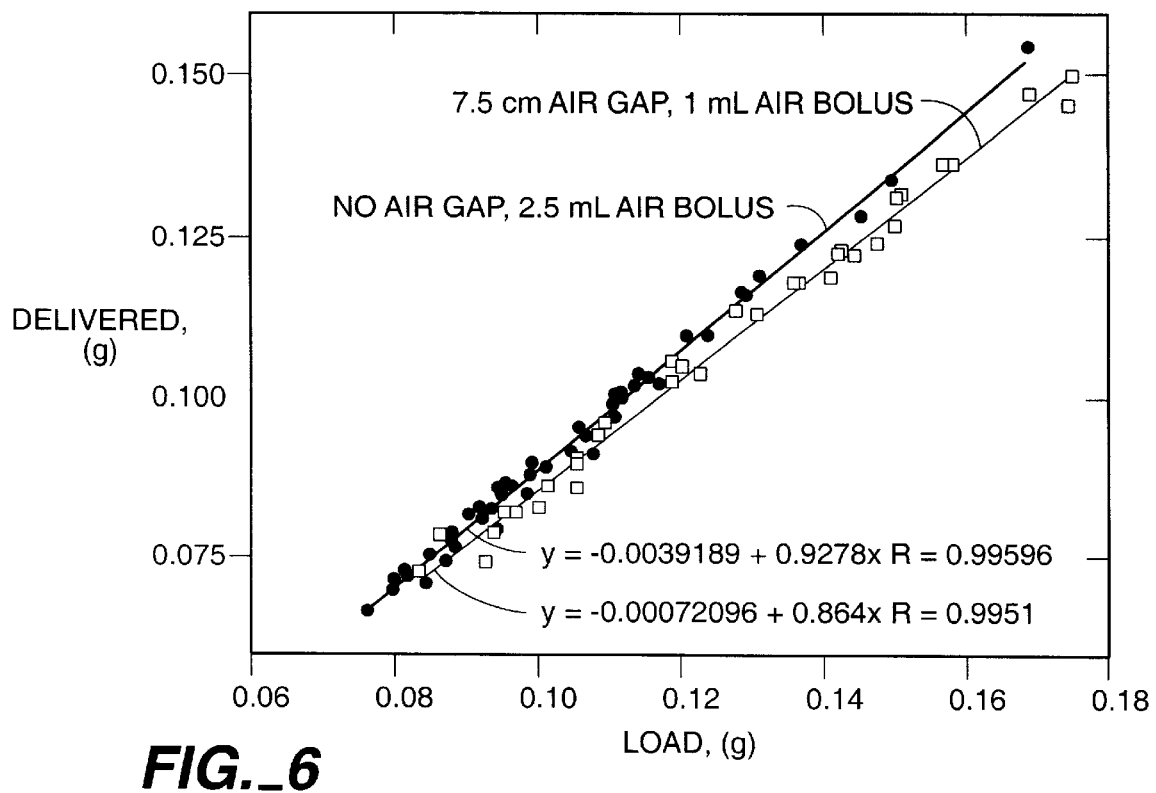
FIG._6
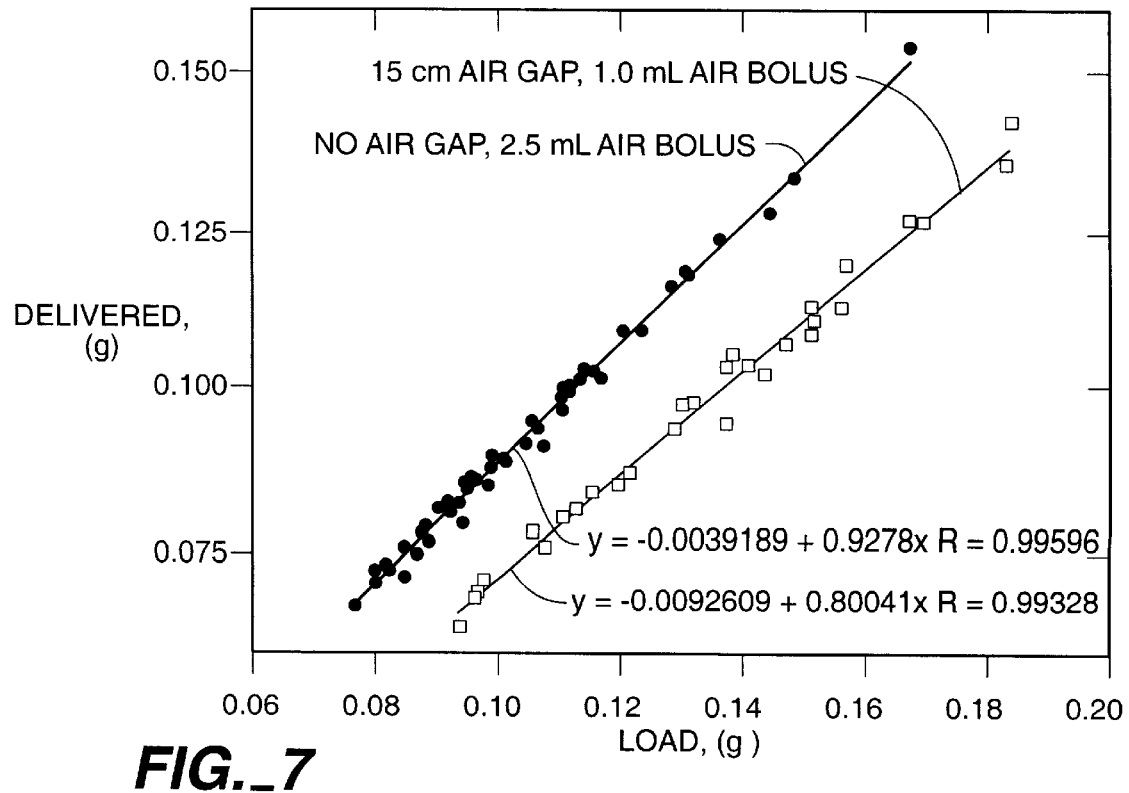
FIG._7

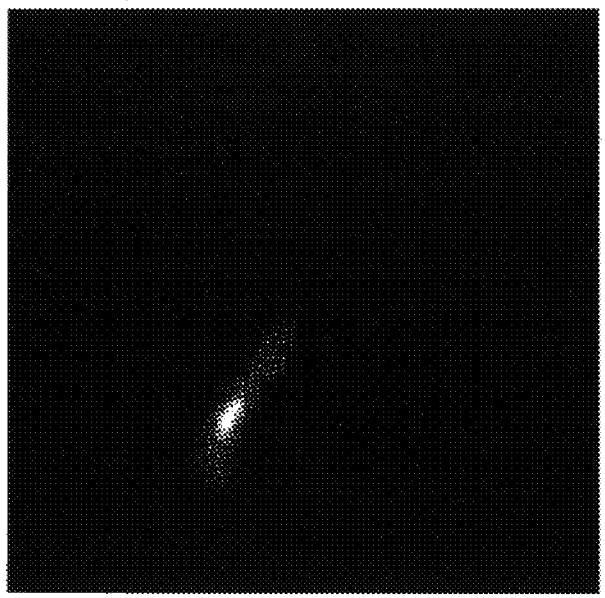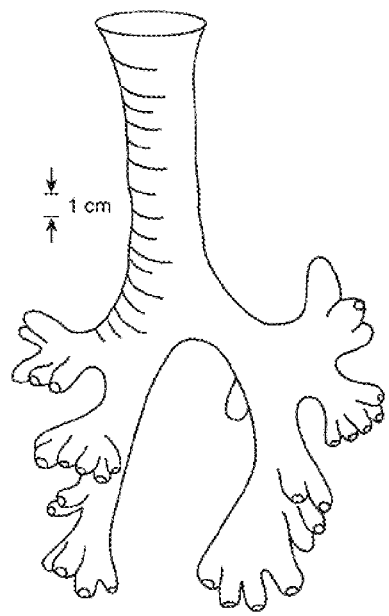
FIG._8

FIG._9

COARSE SPRAY DELIVERY OF FUNCTIONAL BIOLOGIC MATERIAL

This is a continuation, of application Ser. No. 08/439,977 filed May 12, 1995 now abandoned.

FIELD OF THE INVENTION

The present invention is directed to methods and materials useful for delivering functional biologic materials into the pulmonary airways and other body cavities of a subject. The materials to be delivered are prepared having certain characteristics which ensure their delivery and availability without untoward consequences both to the materials or to the subject.

BACKGROUND OF THE INVENTION

It is generally difficult to achieve localization of aerosols in particular sites in the respiratory tract by conventional inhalation via the mouth. [Gonda, *Pharmaceutical Inhalation Aerosol Technology* (Ed. A. J. Hickey), Marcel Dekker, Inc., N.Y., pp. 61–82 (1992)]. Others have employed microspray equipment inserted into airways in animal studies and reported achieving good localization of the delivered dose. [Ferron et al., *J. Aerosol Sci.* 22, S867–S870 (1991); Kreyling et al., *J. Aerosol Sci.* 24, S451–S452 (1993); Hoover et al., *J. Aerosol Med.* 6, 67–72 (1993)]. In order to atomize the liquid they employed compressed air. Although no adverse reactions to the treatment were reported in their experimental animals, application to humans runs the risk of rapid gas expansion inside the airways, a result prudently to be avoided.

Previously, larger volumes of bulk liquid were administered by dripping the material into the airways through a conventional washing pipe that is inserted into the channel of a bronchoscope. However, this method may result in bulk fluid motion into the distal airways and alveoli that would be important to prevent in order to avoid adverse reactions such as inflammation, or infection in the case of gene transfer therapy using viral vectors.

Accordingly, it was an object of the present invention to deliver functional biologic materials in the form of liquid via a bronchoscope in order to achieve well defined localization of such biologic materials in human airways, where they would be expected to be readily available locally with minimal overspill into the alveoli.

SUMMARY OF THE INVENTION

The present invention is directed to a method of delivering functional biologic materials into the lung air passageways of an individual. The salient feature is the delivery of such materials in such manner so as to assure their being deposited via a liquid carrier in the conducting air passageways of the individual. Thus, by the present method the biologic materials, indeed the liquid carrying them, are prevented from reaching the distal airways and alveoli. Thus, the present method ensures the delivery of the therapeutics to a localized region of the lung where they are made available for therapeutic, diagnostic or imaging effect. Yet, because the materials do not reach the distal airways, adverse affects such as inflammation or infection are avoided.

Thus, the present invention is directed to such a method which comprises introducing the biologic materials within a solution or suspension carrier into the airways of an individual in the form of discrete droplets. The droplets have a diameter of greater than about 20 microns and less than about 500 microns, most preferably upwards of about 180 microns. The solution or suspension is delivered at a velocity which is greater than the natural air velocity in the airway during the spontaneous breathing of the individual being treated.

The present invention is directed to a method of delivering functional biologic materials into the pulmonary airways comprising introducing said materials within a solution of suspension into the airways in the form of discrete droplets having a diameter greater than about 20 microns and less than about 500 microns, and at a velocity greater than the natural air velocity in the airway during spontaneous breathing.

The biologic materials comprise classes of compounds that have a known therapeutic effect or diagnostic or imaging function. These compounds may thus be selected from diagnostic agents, imaging agents, growth factors, cytokines, cytostatic and cytotoxic drugs and other anti-cancer agents, anti-inflammatory compounds, antivirals, antibiotics, immunosuppressants and immunostimulators, anesthetics, mucolytic and virolytic compounds, that could be presented as solutions, suspensions or in carriers such as microparticles or nanoparticles. In a preferred embodiment herein, viral vectors harboring genetically engineered gene inserts are introduced via solutions or suspensions. In this manner the gene insert can be absorbed by the individual into the lung cells thus providing a means of gene therapy. However, it will be understood that the present invention is directed to most any biologic material that is available for its known effect.

The delivery of the solution or suspension is in the form of discrete droplets and delivery devices are chosen such that such droplets are formed as such. In the preferred embodiment of the present invention, a conventional washing pipe that has a nozzle at its distal end is used. The nozzle must be shaped in such a manner so as to form the discrete droplets for delivery. The washing pipe is inserted into a bronchoscope that allows a visual control of the location of the delivery in the regions of the lung accessible by the bronchoscope. The relatively large size of the droplets, again ranging from about 20 microns to about 500 microns is considered the reasonable range that assure proper delivery in accordance with the present invention. Again, preferred ranges are just above and below the median of about 180 microns.

The second requirement in accordance with the present invention is that the droplets be delivered at a velocity that exceeds the normal velocity of air during the natural breathing process. In this manner, the droplets are able to resist expulsion until they reach the area of localization. The velocity must not be so rapid as to cause delivery of the droplets into the distal airways and alveoli. Thus, a preferred velocity range would be from about 0.2 m/sec. to about 100 m/sec, and most preferably from about 1 m/sec. to about 50 m/sec. Again, a nozzle and air pressure system is chosen and adjusted so as to meet these dual requirements of discrete droplet formation and velocity during administration.

Although focus has been on upper lung application, it will be understood that the present invention is applicable to the delivery of such biologic materials into other body cavities as well. Such cavities would be expected to be gas filled or temporarily emptied of liquid or solid contents. As examples are the bladder, rectum and empty arteries, using catheters adapted to deliver solutions or suspensions of the appropriate biologic material as a coarse spray for localized delivery and availability.

A typical carrier or vehicle is exemplified by sterile water and glycerol. Reference is suggested to Remington's Pharmaceutical Sciences, 16th Edition (1980 as well as later additions), Physician's Desk Reference published by Medical Economics Data Production Co., Montvale, N.J. and other standard compendia on drug formulation. Generally, the volume of the solution/suspension delivered would range from about 10 to about 2000 $\mu$L.

In a model system in accord with the present invention, large droplet spray (with a droplet size of about 180 microns ($\mu$m), has been produced by rapid expulsion of a viral vector formulation through a nozzle located at the end of a washing pipe that is inserted into the channel of a bronchoscope. Accurate and reproducible dosing of small volumes approximating 40 to 150 microliters was achieved while preserving the integrity of the viral vector for ultimate delivery. The nature of the spray is chosen such that the exposure of the sites distal to the application is substantially minimized. Studies using cascade impaction, human lung casts and rabbits indicate that the method applied to human subjects can be expected to yield deposition of the gene transfer therapy predominantly at the site immediately downstream from the position of the nozzle in the airway. In this work a conventional bronchoscope was used allowing visual control of the location of the delivery. A standard washing pipe was inserted into the bronchoscope channel, it having a nozzle at the distal end that was used for the in situ formation of a spray. The particular equipment used is substantially equivalent to several other available washing pipes marketed in the United States, for example by Olympus America, Inc. which is the distributor of the Olympus PW-6P washing pipe that was used in this particular work. This washing pipe does not incorporate any significant change in design, material, intended use or method of operation that could affect safety and effectiveness when compared with other washing pipes such as those also available from the Olympus America, Inc. source. These washing pipes have been approved by the Food and Drug Administration of the United States.

The relatively large size of the droplets coupled with the relatively high velocity maximizes the deposition of the major part of the spray on the airway walls adjacent to the exit from the nozzle and the first one or two bifurcations of the lung downstream from the locus of application. The reproducibility of the delivery is achieved by employing an electronically actuated system that drives pneumatically the syringe barrel used for the rapid displacement of microliter quantities of liquid therapy through the nozzle.

The dominant deposition mechanism in the proximal generations of human airways is inertial impaction. The efficiency of impaction increases with increasing droplet size and velocity and the composite parameter that controls deposition of droplets in the airway bifurcations is referred to as a Stokes number. See Kim et al., *J. Aerosol Sci.* 25, 567 (1994). An approximate estimate of the likelihood of deposition of the droplets generated by the spray method in the airways can be obtained by use of the research reported by the Kim et al. reference cited immediately above. These researchers presented detailed results of the dependence of droplet deposition on the Stokes number on airway geometry. Using the empirical relationships they derived, it is possible to estimate that for the droplet sizes and velocities (Stokes number greater than about 1) achieved by the equipment used herein in the preferred embodiment, all of the droplets should deposit essentially at the first bifurcation. These researchers also showed that the deposition will further increase in partially obstructed airways such as would be expected to exist for example in cystic fibrosis patients undergoing the gene transfer therapy reported herein.

Distribution of the gene construct formulation after deposition of the spray into distal airways and alveoli could also take place by bulk fluid motion, in particular by gravity-driven flow. For this reason the volume delivered per shot was limited to a maximum of 150 microliters while preserving adequate dosing reproducibility.

DETAILED DESCRIPTION OF THE INVENTION

The present section describes particular details that were employed during the development of the present invention. These details thus represent preferred embodiments, it being understood that the invention is more generically considered in accordance with the disclosure provided supra in respect of the overall description of the present invention. The particular details employed as a preferred embodiment provide sufficient information to enable one skilled in this art to experiment with various equipment, droplet sizes and velocity for different biologic materials, all within the general teachings hereof.

DETAILED DESCRIPTION OF THE DRAWINGS

FIG. 1 shows the configuration of the Kahnetics dosing system with the Olympus washing pipe.

FIG. 2 shows the correlation between the length of the washing pipe loaded and the vehicle weight.

FIG. 3 shows the correlation between the length of the washing pipe loaded and the vehicle weight for the low doses.

FIG. 4 shows the delivery of virus vehicle for anticipated volume loads (80 to 150 microliters).

FIG. 5 shows the delivery of virus vehicle for low volume loads (40 to 80 microliters).

FIG. 6 shows the effect of a 7.5 cm airgap on the delivery of virus vehicle.

FIG. 7 shows the effect of a 15 cm airgap on the delivery of virus vehicle.

FIG. 8 is the anterior view of the distribution of radio label in an idealized human airway cast (left); for comparison a schematic drawing of the cast at the same magnification is shown on the right. The radio label is distributed approximately over the first two generations in the right bronchus just downstream from the position of the spray nozzle.

FIG. 9 is a scintigraphic image of radio label deposited by spray in a live rabbit. The two bright spots are radioactive markers on the surface of the rabbit that are 12 cm apart.

MATERIALS AND METHODS AND EXAMPLES

The following experiments, described in greater detail in subsequent sections, were carried out in order to characterize the performance of the spray system.

Effect of the Spray Equipment on the Vector Survival

It is in principle possible that the use of the equipment for the production of the spray could lead to a significant loss of the viral vector (e.g. due to adsorption in the equipment, or inactivation by the shear forces in the nozzle). The studies reported here show that there is no significant change in the number of plaque forming units in the spray collected in vitro.

Reproducibility of Dosing

It is clearly important to verify that the delivery has adequate accuracy and reproducibility to obtain safe and efficacious therapy. Reproducibility is ~5% by weight per shot.

Droplet Size Distribution by Laser Diffraction

This method has been used and validated extensively for studies of many aerosol generating systems for delivery of the recombinant human deoxyribonuclease (7,8). The droplet size distribution is very narrowly centered around 180 $\mu$m, with less than 1% of the mass of the spray in droplets of size less than 10 $\mu$m.

Cascade Impaction

Although cascade impactors have been built primarily to measure the particle size distributions in "respirable aerosols", i.e., systems containing much smaller droplets than those generated by this method, this technique has been employed to demonstrate the lack of presence of such particles. One of the advantages of this technique compared to the Laser Diffraction is that it simulates the effect of inspiration that could occur while delivering the spray to the airways. The experiments reported below confirm the laser diffraction findings, i.e., that less than 1% by weight of the particles deposits on cascade impactor stages generally associated with "respirable" size range (<7 $\mu$m)

Human Lung Casts

In order to get information on the deposition of the spray in a system that more faithfully represents the geometry of human airways, several human lung cast models have been employed. These models have a limited number of airway generations (up to about 10). Radiolabeled vehicle representative of material that could be used in human therapy was sprayed using the delivery equipment. The label was in the form of $^{99m}$Technetium sulfur colloid that is used as an imaging agent in diagnosis of lung disease. This isotope of Technetium has ideal properties for gamma scintigraphic imaging and a convenient radioactive half life (6 hours). The colloidal nature of the material prevents its absorption from the respiratory tract which is desirable for in vivo studies to identify the size of deposition and subsequent spreading of radioactivity within the respiratory tract as described below.

The location of radioactivity in the casts was determined by gamma scintigraphy, and by measurement of radioactivity in the material escaping the lung cast. The experiments show that the human airway tree is an efficient filter system for the spray produced by this method.

Deposition of the Spray in Anesthetized Rabbits and Rabbit Lung Casts

There are major differences both in the size and the branching pattern between humans and experimental animals such as dogs, rats or rabbits. These animals have monopodial structure with a large direct pathway to parenchyma, in contrast to the more symmetric dichotomous branching system in humans. In rabbits, the pathway length from the airway to the alveoli is therefore likely to be much shorter than in adult humans. Also, the monopodial structure will be less effective at filtering of large particles by intertial impaction as compared to the dichotomous branching structures in humans. The penetration of the spray to small airways and alveoli as studied by deposition of the radiolabel in rabbits should therefore represent the worst experimental model. The results reported here show that less than 1% of the radioactivity appeared to get beyond the first two generations of airways downstream from the location of the spray nozzle. The initial localization of the material deposited by the spray was also verified in experiments with dried rabbit lung casts.

Animals

New Zealand White Rabbits.

Materials

Aliquots of a test virus were stored at −60° C. until use. Each aliquot contained 50 $\mu$L of virus with an initial active concentration of 5.0×10$^9$ pfu/vial (by plaque assay on 293 cells). The number of viral particles (as determined by optical density measurements at 260 nm, OD$_{260}$) per pfu was 100. The virus was stored frozen in a solution containing 10% glycerol, 10 mM MgCl$_2$, 150 mM NaCl, 10 mM Tris, pH 7.8. The test virus used is considered a model system for use in accordance with the present invention. It is a virus that consists of a replication deficient recombinant adenovirus comprising the known (1989) human cystic fibrosis transmembrane conductance regulator gene.

Buffer solutions containing 10 mM Tris, 150 mM NaCl, 10 mM MgCl$_2$, pH 7.8 with or without 10% glycerol were prepared, sterile filtered (0.22 micron Millipore), and stored at room temperature. These solutions were used to simulate various dilutions of the viral solution in the characterization of the spray and during in vivo and in vitro deposition studies.

Radiolabeled $^{99m}$Tc sulfur colloid solutions were obtained from Mallincrodt Medical Inc., San Francisco. The stock $^{99m}$Tc solution was diluted with the 3.3% glycerol virus vehicle solution to adjust radioactivity.

Equipment

A Kahnetics Dispensing System (Bloomington, Calif.) KDS824 Shot Meter was operated with a KDS 6000 Programmable Timer.

Endoscopic Washing Pipes (Olympus, Tokyo, Japan, Model PW-6P) comprised of a luer-lock mouthpiece allowing attachment to a syringe, a main body tubing allowing insertion into a bronchoscope, and a nozzle allowing the liquid to be dispersed in a spray, were used.

A Capintec Radioisotope Calibrator well counter (Ramsey, N.J.), model CRC-12R, Serial No. 12921, was used to quantify the amount of $^{99m}$Tc present in solutions, adhered to filter material from the stages of the cascade impaction analysis, or present inside the lung casts.

A Malvern MasterSizer diffraction analyzer (Malvern Instruments Ltd., Malvern, England) was used to assess the droplet size spectrum produced buy the device.

A low velocity extraction system (HS3000A, Airfiltronix, Congers, N.Y.) was used to remove the aerosol from the rear of the sizing sensing beam in conjunction with the Malvern Instrument.

An 8-stage Non-viable Andersen Mark II Impactor (Atlanta, Ga.) was used to determine the percentage of respirable sized droplets in the spray. Andersen glass fiber filters were placed on the inverted stainless steel collection plates. The flow rate through the impactor was monitored with a Sierra Instruments (Carmel Valley, Calif.) 820 Mass Flow Meter, Model No. 821, Serial No. 3237, range 0–30 SLPM.

A Ludlum Measurement Inc. (Sweetwater, Tex.) Model 3 survey Meter was used to determine the presence of radioactivity on instrumentation.

A Sartorius (McGaw Park, Ill.) BA 4100S balance significant to 0.01 g was used to determine weights during the lung cast and rabbit experiments. A Sartorius (McGaw Park, Ill.) Research R200D semi-microbalance, with readability to 0.01 mg was used for experiments to characterize the performance of the washing pipe.

Orbiter SP+ Single Photon Emission Computerized Tomography (SPECT) gamma camera system (Siemens Medical Systems, Inc., Hoffman Estates, Ill.) was used to obtain scintigraphic images of radiolabeled sprays in lung casts and live rabbits.

Human lung casts from Meditec, Inc. and APM, Inc. were used to assess the localization of the spray in human airways.

An adult 5.5 mm bronchoscope (Olympus) was used to place the Olympus washing pipe in airways.

Microwave oven (General Electric) was used to dry rabbit lungs for preparation of rabbit lung casts.

Endotracheal tubes: Magill 3.0 (Mallincrodt Medical) uncuffed tracheal tube was used to intubate rabbits.

Methods and Results

Characterization of the Olympus Washing Pipe Using the Kahnetics Dispensing System For safety reasons in the clinical practice, it was thought advantageous to avoid loading the washing pipe with quantities of the gene vector construct much larger than the dose to be delivered in one "shot". The syringe attached to the plunger of the metering system was therefore filled with air, and the delivery solution was loaded directly through the nozzle of the washing pipe. In the clinical setting, the washing pipe would then be inserted into the bronchoscope with the tip directed towards the application site. Once activated, the Kahnetics metering system expels 1 to 2.5 mL volume of air loaded in the syringe into the washing pipe. This air bolus expels the solution (or suspension) through the nozzle of the washing pipe producing a spray onto the adjacent lung surfaces. A schematic of this equipment is shown in FIG. 1. Note that the pressure driving the plunger of the metering device (55 psi) is isolated from the air and the liquid in the syringe; the latter are open to atmospheric pressure via the nozzle.

In order to avoid accidental migration of the liquid to the tip of the nozzle, it was decided that following loading of the vehicle, an air gap of up to 15 cm would be inserted between the vehicle and the tip of the washing pipe. This was done by withdrawing further on the 1 c syringe after the tip of the washing pipe was removed from the vehicle reservoir. The effect of loading the washing pipe with an air gap on the delivery of vehicle was then determined.

Experiments were conducted to investigate the reproducibility of loading the washing pipe and the reproducibility of vehicle delivery from the washing pipe. The weight of the empty washing pipe was determined. The tip of the washing pipe was inserted into the vehicle containing 3.3% glycerol. Solution was drawn into the nozzle of the washing pipe by withdrawing on the plunger of a 1 cc syringe attached to the port of the washing pipe. The tip was removed from solution, its surface was wiped dry, and the length of the filled washing pipe was measured to the nearest 0.1 cm. The weight of the loaded washing pipe was then determined. The loaded washing pipe was attached to the Kahnetics 3 cc syringe adapter (preloaded with between a 1 to 2.5 mL air bolus). the Kahnetics "Timed Regulator" knob was set to 55 psi pressure. The shot duration was set at 2 seconds (any value greater than 1 second would have ensured complete expulsion of the air bolus). The finger actuator was depressed to deliver the spray. The spray was delivered into a preweighed plastic 100 mL beaker. The increase in beaker weight was noted.

Results

The correlation between the length of washing pipe filled with vehicle and the subsequent increase in weight is shown in FIG. 2 for volumes ranging from 80 to 150 $\mu$L. A similar graph with volumes ranging from 40 to 90 $\mu$L using a second washing pipe is detailed in FIG. 3. As would be expected in both cases, the amount of vehicle loaded is linearly related to the length of solution drawn into the washing pipe. With the first washing pipe, the slope predicts that 6.8 $\mu$L of vehicle completely fills 1 cm of tubing. Conversely, to load exactly 100 $\mu$L of vehicle, 14.7 cm length of tubing should be filled with solution. Data using another washing pipe reveals that 7.4 $\mu$L of vehicle completely fills 1 cm of tubing. Thus, 13.5 cm of this washing pipe needs to be filled with vehicle to load 100 $\mu$L. Although the variation in the interior diameters of these two washing pipes results in an ≠8% difference in fill volumes, the variation down the length of the washing pipe tubing is much more precise as evidenced by correlation coefficients of 0.9996.

The delivery of vehicle is illustrated in FIG. 4 for the anticipated loads of between 80 to 150 $\mu$L. A 2.5 mL air bolus was used to expel the solution. There is a direct correlation (r=0.996) between the amount of vehicle which is loaded and the amount which is delivered. The delivered volume was a constant 89±3% of the load for volumes ranging from 80 to 150 $\mu$L. (The residual volume, the volume of vehicle which remains behind in the washing pipe, is a constant 11±3% of the load.) For extremely small volume loads between 40 and 80 $\mu$L, the delivered dose is again proportional to the loaded dose (r=0.994, FIG. 5). Although a second washing pipe was used in this instance, and only a 2.0 mL air bolus was used to expel the vehicle, the delivered volume at 89±4% of the load (not shown). Given an 89% delivery, to deliver exactly 100±5 $\mu$L of solution, one should load 112 $\mu$L of vehicle. These data suggest that reproducible small volume deliveries with errors less than 10% are attainable with this technology. The effect of using a 2.0 or 2.5 mL air bolus appears to be negligible.

When an air gap of 7.5 cm was drawn between the vehicle and the washing pipe nozzle, the delivery was still directly proportional to the load (r=0.995) as shown in FIG. 6. A comparison of the slopes indicates that the addition of the 7.5 cm air gap results in slightly lower deliveries. However, the delivery of vehicle was only reduced from 89±3% to 86±3% of the load. Note also that the volume of air used to expel the vehicle was reduced from 2.5 mL to 1.0 mL. The combination of these two effects only reduced the delivery by 3%. Thus, to deliver 100 $\mu$L, approximately 116 $\mu$L of vehicle should be loaded. However, inserting an air gap of 15 cm between the vehicle and nozzle resulted in a larger reduction in delivery (FIG. 7). The delivery was reduced to 73±5% of the vehicle load. Thus, in this case, a load of 137 $\mu$L would be necessary to deliver ~100 $\mu$L.

A protocol was therefore designed for clinical implementation which incorporated the results from the previous experiments. Because the vehicle in the washing pipe could migrate no more than 10 cm, and a 15 cm air gap resulted in substantially lower deliveries, it was recommended that a 10 cm air gap be inserted between the vehicle and the washing pipe nozzle. Additionally, it was recommended that the 3 cc plunger be loaded with 2 mL of air (rather than 1 mL) to reduce residual vehicle from sticking to the walls of the washing pipe.

Laser Diffraction Analysis of the Spray

Method

The droplet size distribution was assessed by Malvern Mastersizer. Because of the pulsed nature of the spray produced by the washing pipe, the Malvern diffraction analyzer was used in the gated threshold mode. This mode allows the instrument to average the size distribution over a period when the aerosol concentration is above a minimum threshold value. The basic procedure involves setting a measurement window with a width considerably longer than the spray pulse, activating the minimum threshold mode and spraying the dose across the measurement zone of the instrument. The droplet size data obtained is then deduced from the average light diffraction pattern over the period when the aerosol concentration is higher than the minimum threshold setting. Threshold obscuration settings of 0.025 and 0.9 were employed for all tests.

The minimum threshold value was chosen to be just above background, the maximum threshold was chosen because it was well above the maximum obscuration generated by the spray. Obscuration is an arbitrary measure of droplet concentration and is based upon the percentage of the incident laser light scattered by the cloud of spray. In these experiments, the lens focal length was 300 mm, appropriate for sizing droplets between 1.2 and 600 microns in diameter. The diffraction data was inverted into the droplet size distribution assuming a relative refractive index of 1.33 and zero optical absorption appropriate for clear aqueous solutions. The model independent fitting routine was used throughout.

For each experiment, the test solution was drawn into the nozzle until 15 cm of the tubing was filled (~115 $\mu$L). About 50 $\mu$L of air was then drawn into the nozzle to ensure that no solution was lost from the nozzle prior to activation. A styrofoam block with a hole the size of the washing pipe was used to position the nozzle at precise locations from the laser beam. The spray was actuated using the Kahnetics dosing system as described above. To determine the stability of the spray emanating from the washing pipe nozzle, the nozzle was initially placed at various distances from the Mastersizer's measurement zone without interfering with the laser beam. This ranged from 2 to 6 cm from the center of the beam. In all subsequent experiments, the nozzle was placed approximately 4 cm from the center of the beam (3 cm from the edge of the beam). The nozzle was also placed exactly 3.5 cm from the front of the receiving lens. The plume from the spray was thus directed across the beam between 1 to 6 cm from the front of the receiving lens. This position was chosen so that the spray was well within the working distance of the lens (7 cm) and to avoid artifacts due to "vignetting" of the diffracted light at the edges. In order to ensure no interference from the spent spray, the Airfiltronix filtration system was used to draw up the effluent aerosol.

Results

Table 1 shows the results of the preliminary experiments with water sprays to ascertain the correct position of the spray with respect to the laser beam. The volume median diameter and span (measure of width of size distribution) are not changed significantly when the nozzle is positioned between 2 and 4 cm from the center of the beam. In all subsequent experiments, the nozzle was placed 4 cm from the center of the lens. Each test solution was sprayed four times and the size characteristics analyzed as before (Table 2). The test solutions represent a range of viscosities that should be typical for therapeutic purposes. The vehicle, with 0%, 3.3%, and 10% glycerol had a volume median diameter of 182, 190 and 205 microns in size (compared to that of 187 microns for water). Importantly, the percent by mass of droplets less than 10 microns in diameter remained low for all vehicles, being 1.1%, 0.9%, and 0.5% respectively, compared to that of 0.6% for water.

TABLE 1

Droplet Size Distribution Versus Nozzle Position for Water, n = 3†

| Distance from the Center of the Beam | Volume Median Diameter ($\mu$m) | Span | % by Weight less than 10 $\mu$m |
|---|---|---|---|
| 2 cm | 191 ± 11 | 1.8 ± 0.2 | 0.9 ± 0.2 |
| 3 cm | 182 ± 5 | 1.7 ± 0.1 | 0.8 ± 0.3 |
| 4 cm | 191 ± 21 | 1.6 ± 0.2 | 0.5 ± 0.5 |
| 6 cm | 152 ± 22 | 1.9 ± 0.4 | 0.8 ± 0.2 |

TABLE 2

Droplet Size Distribution of Various Solutions†

| Test Solution, n = 4 | Volume Median Diameter ($\mu$m) | Span | % by Weight less than 10 $\mu$m |
|---|---|---|---|
| Water | 187 ± 12 | 1.6 ± 0.1 | 0.6 ± 0.4 |
| Vehicle, No Glycerol | 182 ± 5 | 1.8 ± 0.1 | 1.1 ± 0.1 |
| Vehicle, 3.3% Glycerol | 190 ± 9 | 1.7 ± 0.2 | 0.9 ± 0.3 |
| Vehicle, 10% Glycerol | 205 ± 20 | 1.6 ± 0.1 | 0.5 ± 0.3 |

Cascade Impaction Analysis of the Spray

The 8-stage Andersen cascade impactor was used to determine the percentage of the spray present in small respirable sized droplets. Glass fiber filters were placed on each stage to collect the spray. The cut-off diameters for the stages are 10.0, 9.0, 5.8, 4.7, 3.3, 2.1, 1.1, 0.7, and 0.4 microns. The pump, which was calibrated to draw a flow rate of 28.3 L/min, was turned on a few minutes prior to spraying the solution. An in-line mass flow meter (i.e. with readout independent of pressure), between the pump and cascade impactor, monitored the flow rate during the experiment.

The sizing runs were done in triplicate. Approximately 120 $\mu$L of the $^{99m}$Tc sulfur colloid solution was drawn into the nozzle of the washing pipe followed by a 50 $\mu$L air gap to protect against accidental leakage of the solution. The activity of the loaded $^{99m}$Tc solution was determined by inserting the washing pipe into the gamma well counter. The weight of the solution was also recorded. The loaded washing pipe was held vertically with the nozzle aimed downward into the cascade impactor approximately 5 cm from the top stage, at the "lower lip" of the entry orifice. The Kahnetics dispensing system was activated and the $^{99m}$Tc solution was sprayed into the impactor. The residual weight and activity of the $^{99m}$Tc solution in the washing pipe were determined. The filters on each stage were placed in plastic bags and the $^{99m}$Tc activity was measured by gamma well counter. Additionally, swabs of the walls and plates on the top two stages were also made and these tissues were placed into bags and counted.

To determine if attenuation occurred due to the presence of the filters and swabs, up to five additional swabs (paper tissues and alcoholic swabs) were placed into a bag surrounding a tube of $^{99m}$Tc solution; this was the maximum number of tissues and swabs used to wipe any one stage of the impactor with its surrounding walls. The radioactivity was measured before and after addition of the swabs. As a control, the $^{99m}$Tc solution was also sprayed directly into a plastic bag to ensure mass balance of radiolabel (the activity in the bag should equal the activity lost from the washing pipe). To account for decay of the $^{99m}$Tc isotope, the clock time was noted for each measurement. The $^{99m}$Tc isotope has a half life of 5.997 hours. Thus, each activity measurement $A_t$ at time t was normalized relative to the time from the initial activity measurement t0 of the $^{99m}$Tc solution loaded in the washing pipe. The corrected activity, $A_{t0}$, was determined as follows, where (t−t0) is in hours:

$$A_{t_0} = \frac{A_t}{e^{\frac{\ln 0.5 (t-t_0)}{t_{0.5}}}} = \frac{A_t}{e^{-0.11558(t-t_0)}}$$

Results

From an initial loading of the $^{99m}$Tc sulfur colloid solution in the vector vehicle, (120.9±3.7 μL, Tables 3b, 4b, and 5b), approximately 100 μL of the $^{99m}$Tc solution left the washing pipe for the inertial cascade impactor (96.6±2.8 μL, Tables 3b, 4b, 5b). More than 99.6% of the measured radioactivity was found on the top prefilter, corresponding to particles greater than 10 microns in size (Tables 3c, 4c, and 5c). In fact, 99.8 percent of the detected radioactivity was found on the top prefilter and on the first stage (stage 0). Less than 0.2% was found on the filters on the stages which collected droplets less than 9 microns in size. This is entirely consistent with the laser diffraction data which determined that less than 1 percent of the droplets by mass are less than 10 microns in size.

Although 99.6% of the detected radioactivity was present in droplets which had an aerodynamic diameter of greater than 10 microns, the recovery of radioactivity in the cascade impactor was only 91.2±2.7% (Tables 3c, 4c, and 5c). As a control, the same $^{99m}$Tc solution was sprayed into a bag and the radioactivity was measured. A recovery of 99.3 percent was obtained. The loss in radioactivity from the washing pipe, 143.5 μCi, was completely accounted for by that measured into the bag, 142.5 μCi. The unrecovered radioactivity in our cascade impactor experiments may be due to two factors: attenuation during measurement and $^{99m}$Tc solution adhering to and drying on the surface of the top stage. Adding up to five pieces of non-radioactive tissues that were used for swabbing, to a bag with a radioactive vial reduced the measured radioactivity by 2–3%. Thus, attenuation only partially explains the incomplete recovery of radioactivity. The stages of the impactor were then taken apart and a survey meter was passed over each stage. The top stage contained substantial residual radioactivity. This radioactivity could not be removed with either alcohol swabs, or by washing with isopropyl alcohol. Therefore, some of the radioactive colloid material must adhere strongly to the metallic surface. Significantly, no radioactivity was detected on the other stages. These data thus confirm that no more than 0.4% of droplets in the washing pipe spray are less than 10 microns in size. The air flowing through the impactor at 28.3 L/min does not appear to entrain any significant portion of the spray. This suggests that the patient's breathing would be unlikely to affect the spread of the spray delivered directly into the airways.

TABLE 3a

Exp. 1, Loading Washing Pipe with $^{99m}$Tc Solutions †

| Status | Washing Pipe Weight (g) | $^{99m}$Tc (μCi) | $\Delta_t$ (min) | Corrected $^{99m}$Tc (μCi) |
|---|---|---|---|---|
| Unloaded | 10.2049 | 74.0 | 0 | 74.0 |
| Loaded | 10.3257 | 271.0 | 2 | 272.0 |
| After Spraying | 10.2291 | 115.2 | 4 | 116.1 |

†$\Delta_t = t-t_o$ is the time between measuring the $^{99m}$Tc activity in the sample and that in the unloaded washing pipe.

TABLE 3b

Expt. 1, Delivery of the $^{99m}$Tc Solution as a Spray†

| Status | $^{99m}$Tc Solution Volume (μL) | $^{99m}$Tc (μCi) | Corrected $^{99m}$Tc (μCi) |
|---|---|---|---|
| $^{99m}$Tc Loaded | 120.8 μL | 197 μCi | 198.0 |
| $^{99m}$Tc Sprayed | 9.6 μL | 155.8 μCi | 155.9 |

†The volume of $^{99m}$Tc loaded in and sprayed from the washing pipe was calculated from Table 3a, converting weight differences to volumes using a density of 1.0 g/mL.
The $^{99m}$Tc activity and corrected activities were also determined similarly from Table 3a.

TABLE 3c

Expt. 1, Recovery of the $^{99m}$Tc in the Cascade Impactor†

| Impactor Stage | Cut-Off Diameter (μm) | $^{99m}$Tc (μCi) | $\Delta_t$ (min) | Corrected $^{99m}$Tc (μCi) | % $^{99m}$Tc Recovered |
|---|---|---|---|---|---|
| Wipe, Stage O | 10.0 | 135.3 | 21 | 140.9 | 90.4 |
| Second Wipe | 10.0 | 2.5 | 26 | 2.6 | 1.7 |
| Wipe and Wash | 10.0 | 2.9 | 40 | 3.1 | 2.0 |
| Plate 1 | 9.0 | 0.13 | 27 | 0.14 | <0.1 |
| Plate 2 | 5.8 | BKG | 28 | BKG | |
| Plate 3 | 4.7 | BKG | 29 | BKG | |
| Plate 4 | 3.3 | BKG | 30 | BKG | |
| Plate 5 | 2.1 | 0.1 | 31 | 0.1 | <0.1 |
| Plate 6 | 1.1 | 0.1 | 32 | 0.1 | <0.1 |
| Plate 7 | 0.7 | BKG | 32 | BKG | |
| Plate 8 | 0.4 | BKG | 33 | BKG | |
| Filter | NA | 0.05 | 34 | 0.05 | <0.1 |
| Recovery | | 141.08 | | 147.50 | 94.3% |

†The activity of $^{99m}$Tc was corrected to account for decay from the time of the initial activity measurements to that of the samples' activity measurements.
The corrected amount of $^{99m}$Tc found on each stage was divided by the amount of delivered $^{99m}$Tc (from Table 3b, 155.9 μCi) to yield the percent $^{99m}$Tc recovered. BKG represents an activity equal to that of the background.

TABLE 4a

Expt. 2, Loading the Washing Pipe with the $^{99m}$TC Solution†

| Status | Washing Pipe Weight (g) | $^{99m}$Tc (μCi) | $\Delta_t$ (min) | Corrected $^{99m}$Tc (μCi) |
|---|---|---|---|---|
| Unloaded | 10.2048 | 77.6 | 0 | 77.6 |
| Loaded | 10.3294 | 255.0 | 2 | 256.0 |
| After Spraying | 10.2300 | 111.5 | 4 | 112.4 |

†$\Delta_t = t-t_o$ is the time between measuring the $^{99m}$Tc activity in the sample and that in the unloaded washing pipe.

TABLE 4b

Expt. 2, Delivery of the $^{99m}$Tc Solution as a Spray†

| Status | $^{99m}$Tc Solution Volume (µL) | $^{99m}$Tc (µCi) | Corrected $^{99m}$Tc (µCi) |
|---|---|---|---|
| $^{99m}$Tc Loaded | 124.6 | 177.4 | 178.4 |
| $^{99m}$Tc Sprayed | 99.4 | 143.5 | 143.6 |

†The volume of $^{99m}$Tc loaded in and sprayed from the washing pipe was calculated from Table 4a, converting weight differences to volumes using a density of 1.0 g/mL.
The $^{99m}$Tc activity and corrected activities were also determined similarly from Table 4a.

TABLE 4c

Expt. 2, Recovery of $^{99m}$Tc in the Cascade Impactor†

| Impactor Stage | Cut-Off Diameter (µm) | $^{99m}$Tc (µCi) | $\Delta_t$ (min) | Corrected $^{99m}$Tc (µCi) | % $^{99m}$Tc Recovered |
|---|---|---|---|---|---|
| Wipe, Stage 0 | 10.0 | 124.3 | 9 | 126.5 | 88.1 |
| Second Wipe | 10.0 | 1.4 | 13 | 1.4 | 1.0 |
| Plate 1 | 9.0 | 0.1 | 16 | 0.1 | <0.1 |
| Plate 2 | 5.8 | BKG | 17 | BKG | |
| Plate 3 | 4.7 | 0.1 | 18 | 0.1 | <0.1 |
| Plate 4 | 3.3 | BKG | 19 | BKG | |
| Plate 5 | 2.1 | 0.15 | 20 | 0.16 | 0.1 |
| Plate 6 | 1.1 | BKG | 21 | BKG | |
| Plate 7 | 0.7 | BKG | 22 | BKG | |
| Plate 8 | 0.4 | BKG | 23 | BKG | |
| Filter | NA | BKG | 24 | BKG | |
| Recovery | | 126.05 | | 128.3 | 89.3% |

†The activity of the $^{99m}$Tc was corrected to account for decay from the time of the initial activity measurements to that of the samples' activity measurements.
The corrected amount of $^{99m}$Tc found on each stage was divided by the amount of delivered $^{99m}$Tc (from Table 4b, 143.6 µCi) to yield the percent $^{99m}$Tc recovered. BKG represents an activity equal to that of the background.

TABLE 5a

Expt. 3, Loading the Washing Pipe with the $^{99m}$Tc Solution†

| Status | Washing Pipe Weight (g) | $^{99m}$Tc (µCi) | $\Delta_t$ (min) | Corrected $^{99m}$Tc (µCi) |
|---|---|---|---|---|
| Unloaded | 10.2076 | 85.2 | 0 | 85.2 |
| Loaded | 10.3248 | 228.0 | 2 | 228.9 |
| After Spraying | 10.2310 | 118.0 | 4 | 118.9 |

†$\Delta_t = t-t_o$ is the time between measuring the $^{99m}$Tc activity in the sample and that in the unloaded washing pipe.

TABLE 5b

Expt. 3, Delivery of the $^{99m}$Tc Solution as a Spray†

| Status | $^{99m}$Tc Solution Volume (µL) | $^{99m}$Tc (µCi) | Corrected $^{99m}$Tc (µCi) |
|---|---|---|---|
| $^{99m}$Tc Loaded | 117.2 | 142.8 | 143.7 |
| $^{99m}$Tc Sprayed | 93.8 | 110.0 | 110.0 |

†The volume of $^{99m}$Tc loaded in and sprayed from the washing pipe was calculated from Table 5a, converting weight differences to volumes using a density of 1.0 g/mL.
The $^{99m}$Tc activity and corrected activities were also determined similarly from Table 5a.

TABLE 5c

Expt. 3, Recovery of $^{99m}$Tc in the Cascade Impactor†

| Impactor Stage | Cut-Off Diameter (µm) | $^{99m}$Tc (µCi) | $\Delta_t$ (min) | Corrected $^{99m}$Tc (µCi) | % $^{99m}$Tc Recovered |
|---|---|---|---|---|---|
| Wipe, Stage 0 | 10.0 | 95.5 | 13 | 97.9 | 89.0 |
| Second Wipe | 10.0 | 0.7 | 16 | 0.7 | 0.64 |
| Plate 1 | 9.0 | 0.2 | 19 | 0.2 | 0.18 |
| Plate 2 | 5.8 | BKG | 19 | BKG | |
| Plate 3 | 4.7 | 0.05 | 20 | 0.05 | <0.1 |
| Plate 4 | 3.3 | BKG | 21 | BKG | |
| Plate 5 | 2.1 | BKG | 22 | BKG | |
| Plate 6 | 1.1 | 0.05 | 23 | 0.05 | <0.1 |
| Plate 7 | 0.7 | 0.05 | 24 | 0.05 | <0.1 |
| Plate 8 | 0.4 | BKG | 25 | BKG | |
| Filter | NA | BKG | 26 | BKG | |
| Recovery | | 96.55 | | 98.95 | 90.0% |

†The activity of the $^{99m}$Tc was corrected to account for decay from the time of the initial activity measurements to that of the samples' activity measurements.
The corrected amount of $^{99m}$Tc found on each stage was divided by the amount of delivered $^{99m}$Tc (from Table 5b, 110.0 µCi) to yield the percent $^{99m}$Tc recovered. BKG represents an activity equal to that of the background.

Effect of Spraying on the Survival of the Adenovirus Vector

Method

Experiments were performed to determine the effect of spraying the effective adenovirus through the washing pipe, designed to mimic the clinical protocol (Appendix II).

Vials containing 50 µL aliquots of the test virus, in a solution containing 10% glycerol, 10 mM MgCl$_2$, 150 mM NaCl, 10 mM Tris, pH 7.8 were stored at or below −60° C. The initial active virus concentration was 5.0×10$^{10}$ pfu/mL (by plaque assay on 293 cells). The number of viral particles (as determined by optical density at 260 nm, OD$_{260}$) was 5.0×10$^{12}$ pu/mL. Thus the ratio of particles to pfu was 100. A retitration of the original stock when the samples from these spray experiments were assayed yielded 1.0×10$^{10}$ pfu/mL and 3.6×10$^{12}$ pu/mL; this titer was used in the final calculations.

Just prior to use, the stock virus vials were thawed out and stored on ice. Vehicle solution identical to that of the virus solution except containing only 3.3% glycerol was used throughout as dilution buffer. The buffer in the spray collection containers was identical to that of the stock virus solutions. The high dose virus solution at nominal concentration of 5×10$^9$ pfu/mL was prepared by a ten fold dilution of virus stock into the dilution buffer. The low dose virus solution at nominal concentration of 1×10$^7$ pfu/mL was prepared by diluting the virus stock sequentially into dilution buffer using first a one hundred fold dilution, followed by a 10 fold dilution and finally a five fold dilution. The diluted virus was stored on ice until use. Cryovials (1.8 mL) were filled with 0.9 mL of the collection buffer and weighed.

On two separate occasions, three experiments were performed on both the low dose and high dose virus solutions. All of the experiments with the low dose virus solutions were performed prior to those with the high dose virus solutions. This was done in case the virus was lost due to adsorption onto the washing pipe tubing. If a small amount of virus did adsorb, this loss would be more readily observed in the experiments with the low dose virus solutions. The tip of the washing pipe nozzle was placed in the low dose virus solution. The virus solution was drawn into the nozzle of the washing pipe approximately 17 cm down the length of the tube by drawing back on a 1 cc plunger attached to the luer-lock port of the washing pipe. After removing the washing pipe tip from the virus solution, the plunger was withdrawn further until an air gap of ~50 µL was drawn into the tip. This prevented virus solution from dripping out the nozzle of the washing pipe prior to actuation. The washing pipe was attached to the Kahnetics dosing system. The nozzle was directed into the prefilled cryovial and the spray was actuated. The cryovial was weighed to determine the volume of delivered virus solution. After gentle mixing, the contents of the cryovial were aliquoted into three tubes, and stored frozen, at or below −60° C.

Additionally, control experiments were performed to determine if the virus survival was affected by being stored on ice, after being thawed and diluted, for the duration of the experiment. After preparation of the virus dilutions and before initiating the spray experiments, time zero controls were prepared. To two cryovials prefilled with 0.9 mL collection buffer, 0.1 mL of either the low dose or high dose virus solution was aliquoted. The quantity of the aliquot was determined by weight difference. Each of these vials was gently mixed, divided into three tubes, and stored frozen, at or below −60 ° C. At the completion of the experiment (~75 minutes duration), a 0.1 mL aliquot from both the low and high dose virus solutions was again nixed into the cryovial filled with 0.9 mL of collection buffer. The exact solution quantity was determined by weight difference. Again, the solutions were divided into triplicates, and stored frozen, at or below −60° C. All of the triplicate vials, both experimental and controls, were shipped on dry ice for subsequent analysis.

Results

The effect of spraying the low dose virus is presented in Table 6. The two control virus solutions which were not sprayed but which were thawed and diluted along with the experimental samples registered between 50–100% (1.0–2.0×10$^5$ pfu/mL) of the anticipated virus count (~2.0× 10$^5$ pfu/mL). Given the variability in this assay, these numbers show that the virus was unaffected by the freezing, thawing and shipping procedures. The first control was frozen prior to initiation of the experiment while the second control was frozen at the completion of the experiment. No significant difference was observed between these two controls indicting that virus survival was not affected by being stored thawed on ice for the 75 minute duration of the experiment.

The three sprayed virus samples assayed between 40–200% (1.0–5.0×10$^5$ pfu/mL) of the anticipated virus count (~2.5×10$^5$ pfu/mL). These assays indicate that virus survival was unaffected by being sprayed through, or being in contact with, the washing pipe at a dose of approximately 2×10$^6$ pfu/mL.

The two high dose virus controls yielded virus plaque forming units at between 43 and 76% of anticipated (Table 7a). The difference between the two controls is within the assay variation, thus indicating that the virus was not inactivated solely by remaining thawed for the duration of the experiment. The difference from the anticipated value may indicate some loss in virus survival during freeze/thawing and/or the shipping process prior to assay.

The samples which were sprayed registered 16 to 41% of the anticipated viral survival counts. From comparison with the two control samples (43–70% of expected value), it is possible that up to 50% of the virus at 1×10$^9$ pfu/mL could be inactivated by spraying. However, given the assay variation, and that the assay reports discontinuous values from dilution steps, it is entirely possible that very little, if any, inactivation occurs.

The number of virus particles was assayed only at the high virus concentration due to assay sensitivity. The control samples assayed at between 64 and 81% of their expected values (Table 7b). The sprayed virus samples assayed at between 62 and 97% of their expected values. The overlapping ranges indicates that no difference exists between the control and sprayed samples. Thus, the number of virus particles was unaffected by being sprayed through the washing pipe indicating that no significant adsorption of virus particles on the washing pipe occurred.

TABLE 6

Survival of the Low dose Virus Following Spraying†

| Solution | Label | Delivered Volume, (µL) | Dilution Factor | Expected Virus Count pfu/mL | Measured Virus Count, pfu/ml | | |
|---|---|---|---|---|---|---|---|
| | | | | | Trial #1 | Trial #2 | Trial #3 |
| Neg. Control | CBC | NA | NA | 0 | 0 | 0 | 0 |
| Cont., T = 0 min | LDC-1 | 101.9 | 0.102 | 2.0 × 10$^5$ | 1.5 × 10$^5$ | 1.0 × 10$^5$ | 2.0 × 10$^5$ |
| Control, T = 75 | LDC-2 | 98.5 | 0.099 | 2.0 × 10$^5$ | 1.0 × 10$^5$ | 1.5 × 10$^5$ | 1.5 × 10$^5$ |
| First Spray | NDL-1 | 126.5 | 0.123 | 2.5 × 10$^5$ | 5.0 × 10$^5$ | 5.0 × 10$^5$ | 1.0 × 10$^5$ |
| Second Spray | NDL-2 | 125.3 | 0.122 | 2.4 × 10$^5$ | 5.0 × 10$^5$ | 5.0 × 10$^5$ | 1.4 × 10$^5$ |
| Third Spray | NDL-3 | 128.3 | 0.125 | 2.5 × 10$^5$ | 3.0 × 10$^5$ | 3.0 × 10$^5$ | 1.5 × 10$^5$ |
| Cont., T = 0 min | LDC-3 | 105.6 | 0.105 | 2.1 × 10$^5$ | 1.5 × 10$^5$ | 1.5 × 10$^5$ | ND |
| Control, T = 30 | LCD-4 | 105.8 | 0.105 | 2.1 × 10$^5$ | 1.8 × 10$^5$ | 1.6 × 10$^5$ | ND |
| First Spray | NDL-4 | 125.7 | 0.123 | 2.5 × 10$^5$ | 1.3 × 10$^5$ | 1.5 × 10$^5$ | ND |

TABLE 6-continued

Survival of the Low dose Virus Following Spraying†

| Solution | Label | Delivered Volume, (μL) | Dilution Factor | Expected Virus Count pfu/mL | Measured Virus Count, pfu/ml | | |
|---|---|---|---|---|---|---|---|
| | | | | | Trial #1 | Trial #2 | Trial #3 |
| Second Spray | NDL-5 | 124.3 | 0.121 | $2.4 \times 10^5$ | $1.0 \times 10^5$ | $1.0 \times 10^5$ | ND |
| Third Spray | NDL-6 | 125.5 | 0.122 | $2.4 \times 10^5$ | $1.0 \times 10^5$ | $1.0 \times 10^5$ | ND |

†The delivered volume is calculated by dividing the delivered weight of virus solution by a density of 1.0 g/mL. Given an initial virus concentration of $1 \times 10^{10}$ pfu/mL, the low dose stock would be $2.0 \times 10^5$ pfu/mL. The delivered volume is diluted into 0.9 mL. The dilution factor is thus calculated by dividing the delivered volume by the sum of the delivered volume plus 0.9 mL. If exactly 100 μL was delivered, a dilution factor of 0.1 would result. The expected virus count is then determined by multiplying the dilution factor by $2 \times 10^5$ pfu/mL.
ND = not determined.

TABLE 7a

Survival of the High Dose Virus Following Spraying†

| Solution | Label | Delivered Volume (μL) | Dilution Factor | Expected Virus Count pfu/mL | Measured Virus Count, pfu/mL | |
|---|---|---|---|---|---|---|
| | | | | | Trial #1 | Trial #2 |
| Neg. Control | CBC-1 | NA | NA | 0 | 0 | 0 |
| Cont., T = 0 min | HDC-1 | 101.0 | 0.101 | $10.5 \times 10^7$ | $5.0 \times 10^7$ | $6.0 \times 10^7$ |
| Control, T = 75 | HDC-2 | 98.1 | 0.098 | $10.5 \times 10^7$ | $4.5 \times 10^7$ | $8.0 \times 10^7$ |
| First Spray | NDH-1 | 126.9 | 0.124 | $12.3 \times 10^7$ | $5.0 \times 10^7$ | $2.5 \times 10^7$ |
| Second Spray | NDH-2 | 127.4 | 0.124 | $12.1 \times 10^7$ | $5.0 \times 10^7$ | $4.0 \times 10^7$ |
| Third Spray | NDH-3 | 123.2 | 0.120 | $12.2 \times 10^7$ | $2.0 \times 10^7$ | $2.0 \times 10^7$ |

†The delivered volume is calculated by dividing the delivered weight of virus solution by a density of 1.0 g/mL. Given an initial virus concentration of $1 \times 10^{10}$ pfu/mL, the high dose stock would be $1.0 \times 10^9$ pfu/mL. The delivered volume was diluted into 0.9 mL. The dilution factor is thus calculated by dividing the delivered volume by the sum of the delivered volume plus 0.9 mL. If exactly 100 μL was delivered, a dilution factor of 0.1 would result. The expected virus count is then determined by multiplying the dilution factor by $1 \times 10^9$ pfu/mL

TABLE 7b

Particle Counts of the High Dose Virus Following Spraying†

| Solution | Label | Delivered Volume, (μL) | Dilution Factor | Expected # of Particles pu/mL | Measured # of Particles, pu/mL | |
|---|---|---|---|---|---|---|
| | | | | | Trial #1 | Trial #2 |
| Neg. Control | CBC-1 | NA | NA | 0 | 0 | 0 |
| Cont., T = 0 min | HDC-1 | 101.0 | 0.101 | $2.6 \times 10^{10}$ | $1.8 \times 10^{10}$ | $2.1 \times 10^{10}$ |
| Control, T = 75 | HDC-2 | 98.1 | 0.098 | $2.5 \times 10^{10}$ | $1.7 \times 10^{10}$ | $1.6 \times 10^{10}$ |
| First Spray | NDH-1 | 126.9 | 0.124 | $3.2 \times 10^{10}$ | $2.6 \times 10^{10}$ | $3.1 \times 10^{10}$ |
| Second Spray | NDH-2 | 127.4 | 0.124 | $3.2 \times 10^{10}$ | $3.0 \times 10^{10}$ | $2.0 \times 10^{10}$ |
| Third Spray | NDH-3 | 123.2 | 0.120 | $3.1 \times 10^{10}$ | $2.3 \times 10^{10}$ | $2.7 \times 10^{10}$ |

†The delivered volume is calculated by dividing the delivered weight of virus solution by a density of 1.0 g/mL. Given an initial virus particle count of $3.6 \times 10^{12}$ pu/mL, the high dose stock would be $2.6 \times 10^{11}$ pu/mL. The delivered volume was diluted into 0.9 mL. The dilution factor is thus calculated by dividing the delivered volume by the sum of the delivered volume plus 0.9 mL. If exactly 100 μl was delivered a dilution factor of 0.1 would result. The expected virus count is then determined by multiplying the dilution factor by $2.6 \times 10^{11}$ pu/mL.

Experiments with Human Lung Casts

Two types of hollow human lung casts were used to simulate the delivery of the adenovirus vector to the airways (Table 8). Both are routinely used to teach bronchoscopy. The first cast (Meditech, Inc., Watertown, Mass.) is an idealized cast of the first 5–6 generations of human airways. The second cast (ALM II; APM Inc., Raleigh, N.C.) is derived from accurate casts of human airways. It is thus more anatomically correct for the first 5–8 generations of the airways. The final airway generation had holes corresponding to their airway diameter.

TABLE 8

Hollow Casts of Human Airways

| | Idealized | Realistic |
|---|---|---|
| Source | Meditech, Inc. | APM Inc. |
| Tracheal Diameter | 20 mm | 18 mm |
| Tracheal Length | 128 mm | 104 mm |
| Right. Main Bronchial Length | 35 mm | 33 mm |
| Left. Main Bronchial Length | 37 mm | 53 mm |
| Maximum Number of Airway Generations | 6 | 8 |
| Terminal Airway Diameter | 3 mm | 2 mm |

To test the distribution of the spray in these model airways, we first labeled the vehicle that could be used for therapy with $^{99m}$Tc-sulfur colloid. With the radiolabeled medium, we could measure the distribution of the spray throughout the casts by gamma camera imaging as well as to determine the fraction of the spray that is not captured within the cast. To measure the latter, we secured plastic bags around all of the exiting airways and measured the amount of radioactivity within the bags in a gamma well counter.

Three separate experiments were performed in each cast. First we loaded via the nozzle 75–100 μL of the $^{99m}$Tc-labelled solution into the Olympus washing pipe. The preloaded pipe was weighed and the amount of radioactivity within the pipe determined in the gamma well counter. The washing pipe was then attached to a 3 mL plastic syringe containing 2 mL of air. The barrel of the syringe was attached to the Kahnetics metering system. The system parameters were 55 psi, and a shot duration of 2 seconds; these are the parameters used in the other in vitro studies reported here. Once loaded, plastic bags were secured around the lung cast so that no radioactivity could escape the cast. The cast was placed under the gamma camera and the bronchoscope was used to locate the entrance to a main stem bronchus. The tip of the bronchoscope was positioned just beyond the carina into the right main stem bronchus. The washing pipe was threaded through the operating channel of the bronchoscope until the tip of the pipe could just be seen exiting the scope. A gamma camera image of the radioactivity in the washing pipe was taken to obtain the initial location of the washing pipe inside the cast. The shotmeter was then activated to deliver the spray, the washing pipe was withdrawn into the bronchoscope, and the bronchoscope was removed from the lung cast. A second gamma camera image was obtained of the distribution of the spray throughout the cast.

After the washing pipe was removed from the lung cast, its weight and radioactivity content were again measured to determine the volume and amount of radioactivity delivered to the lung cast. The washing pipe was reloaded with $^{99m}$Tc solution and the delivery was repeated this time into the left main stem bronchus. After this second delivery, the plastic bags were removed from the cast and the amount radioactivity exiting the right or left lung was determined.

Results

Examples of one of the images following the delivery of the spray into the idealized cast together with the schematic drawing of the cast are shown in FIG. 8 (the image and the drawing are approximately at the same magnification and same orientation, i.e., with the right lung appearing on the left side of the figures; the radioactivity is located at the first two generations in the right bronchus). Note that the spray distributes over about 2 generations of airways in this example. The total distance that the bulk of the spray traveled from the tip of the washing pipe into the airways is about 5 cm. The surface area over which the spray deposits can be estimated from anatomical models to be around 20 cm$^2$.

The results on the escape of radioactivity from the lung cast are shown in Tables 9 and 10. It can be seen that the majority of the radioactivity was retained within the lung casts. We noted no significant differences between the two types of casts. Overall (data from both types of lung casts combined) 82±8 μl of fluid was delivered and only 0.6±0.3% of that fluid exited the smallest airways of the cast.

TABLE 9

Idealized Lung Cast

| Experiment | Lung | μl Delivered | μCi Delivered | % Exiting Cast |
|---|---|---|---|---|
| 1 | Right | 86 | 444 | 0.66 |
| 2 | Right | 86 | 235 | 0.05 |
| 3 | Right | 85 | 213 | 2.02 |
| 1 | Left | 92 | 486 | 0.27 |
| 2 | Left | 65 | 171 | 0.30 |
| 3 | Left | 93 | 275 | 2.24 |
|  |  |  | MEAN | 0.9 |
|  |  |  | SD | 0.4 |

TABLE 10

Realistic Lung Cast

| Experiment | Lung | μl Delivered | μCi Delivered | % Exiting Cast |
|---|---|---|---|---|
| 1 | Right | 87 | 525 | 0.06 |
| 2 | Right | 74 | 236 | 0.19 |
| 3 | Right | 75 | 210 | 0.09 |
| 1 | Left | 86 | 539 | 0.05 |
| 2 | Left | 73 | 150 | 0.45 |
| 3 | Left | 77 | 223 | 0.16 |
|  |  |  | MEAN | 0.2 |
|  |  |  | SD | 0.1 |

Experiments with Dried Rabbit Lungs

Method

Since for example in gene transfer therapy, the biologic agent may have to be delivered to smaller airways than could adequately test in human airway models, a lung cast from a rabbit lung was made. The lungs from a 3.4 kg rabbit were obtained, inflated to 30 cm H$_2$O, airway pressure, and dried for 1 hour on the lowest power in a microwave oven.

Once dry, the parenchyma from the right lung was carefully removed with forceps leaving behind the hollow airway skeleton of the central airways of the rabbit. Approximately 10 generations of airways, smallest diameter <0.5 mm, remained. The trachea of the rabbit is of similar size as the airways into which the adenoviral vector will be placed in humans (5.5 mm). This lung cast represents the "worst case" scenario of deposition beyond small airways.

For these studies a smaller volume (52±9 μl, mean ±SD, n=5) was used to deliver these smaller volumes to rabbits in vivo. Five experiments in this lung model using the same procedure as the one described for the human lung casts were carried out except that a bronchoscope was not used to place the tip of the washing pipe inside the cast. Instead, visual observation was used through the translucent dried airway wall the placement of the metal tip. The tip of the washing pipe was placed just into the right mainstem bronchus (the airway skeleton) and the $^{99m}$Tc-sulfur colloid solution was delivered to the cast with the Kahnetics metering system operating under the same conditions as described in the previous section and to be used clinically. A gamma camera image of the distribution of the spray was obtained. The volume and amount of radioactivity delivered to the lung cast was determined by weighing and measuring the radioactivity content of the washing pipe before and after the delivery.

Results

The results of these experiments are shown in Table 11. Compared to the human lung casts, the spray was delivered to smaller sized airways. In this rabbit lung cast, the radioactivity was found to be confined over a shorter distance (~2 cm) with a correspondingly smaller surface area (estimated from anatomical models to be about 5 cm²) than in the human lung cast models. Importantly, in the rabbit model as in the human model, except for one run, less than 1% (mean 0.71%, SD 1.51) of the spray exited the terminal airways. As outlined previously, the rabbit model due to its geometry represents the worst possible case compared to the situation in adult human airways in terms of the potential of the spray escaping downstream beyond the desired location.

TABLE 11

Distribution of the Spray Using Dried Rabbit Lung Cast

| Experiment # | μL Delivered | μCi Delivered | % Exiting Cast |
|---|---|---|---|
| 1 | 41 | 40 | 0 |
| 2 | 43 | 16 | 3.4 |
| 3 | 57 | 22 | 0 |
| 4 | 60 | 176 | 0.03 |
| 5 | 56 | 164 | 0.11 |
|  |  | MEAN | 0.71 |
|  |  | SD | 1.51 |

In Vivo Rabbit Experiments

Method

Experiments were performed in 5 rabbits (3.3±0.1 kg body weight) to examine the distribution of the spray within the living rabbit lung and the redistribution of the spray over time. Since the airways in live animals as in humans are coated with mucus and ciliated epithelium, we wished to investigate if there was a risk that particles deposited on the surface would redistribute overtime by retrograde movement into the alveoli, as opposed to the desirable natural clearance mouthward by mucociliary transport. To both assess the distribution of the spray within the airways by gamma cameral imaging, and the redistribution over time, the vehicle was labelled with the imaging and diagnostic material with $^{99m}$Tc-sulfur colloid. The loaded washing pipe was preweighed and the amount of radioactivity contained within it measured. Each rabbit was anesthetized with ketamine (55 mg/kg) and xylazine (5 mg/kg) by intramuscular injection. Radioactive markers were placed on the chest of the rabbits as reference points for imaging the chest wall. The rabbit was intubated with a 3.0 Nagill endotracheal tube. The tube was secured to the upper jaw of the rabbit. In a previous experiment in a dead rabbit, the distance from the mouth-end of the endotracheal tube to the entrance of the main-stem bronchi (18 cm) was measured. For the experiment in the live rabbit, the tip of the washing pipe was guided into the endotracheal tube 20 cm into the lung. No attempt was made to place the tip in either the right or left mainstem bronchus. For these experiments, the tip was advanced such that it was likely to be well beyond the main bronchi. The spray was delivered, the amount delivered was measured by reweighing the washing pipe and measuring its radioactivity post-delivery. The chest of the rabbit was imaged in the supine position at various intervals up to 24 hours post delivery. The relative amount of radioactivity remaining in the lungs was determined by quantifying the gamma camera images, correcting for radioactive decay of the isotope, and calculating the % of the original radioactivity remaining in the lung over time.

Results 5.0±3.1 μl of $^{99m}$Tc-sulfur colloid solution was delivered. The initial deposition and residual radioactivity at different times are shown in Tables 12 and 13.

From the gamma camera images, it appeared that the spray was initially localized over a distance of 3–4 cm that, from anatomical models (11) corresponds to a surface area of 3–5 cm². These images resembled the images from the rabbit lung casts, indicating that the spray deposited in a localized area in the vicinity of the site of the deposition as shown in FIG. 9. The two bright spots on this image are two radioactive standards placed on the rabbit chest wall 12 cm apart.

Some of the radioactivity (up to 20%) cleared very rapidly by mucociliary clearance. The majority remained localized and cleared much more slowly. On average, 72% of the spray remained localized after 24 hours. Since the rabbit clears particles with half times much longer than man, we do not think this represents alveolar deposition of the particles but rather slow airway clearance. Rapid decay of the isotope prevented further monitoring of the clearance kinetics of the particles.

TABLE 12

Delivery of The Microspray to Rabbits

| Animal # | Body weight (kg) | mL Delivered | μCi Delivered |
|---|---|---|---|
| 9 | 3.1 | 54 | 373 |
| 10 | 3.2 | 43 | 298 |
| 11 | 3.4 | 43 | 400 |
| 12 | 3.4 | 53 | 380 |
| 10B | 3.4 | 59 | 540 |

TABLE 13

% Delivered Activity Remaining in the Lungs in Rabbits In vivo

| Time (min) | 9 | 10 | 11 | ANIMAL 12 | # 10B | MEAN | SD |
|---|---|---|---|---|---|---|---|
| 5 | — | 87 | 100 | 86 | 97 | 93 | 7 |
| 10 | — | 85 | 90 | 85 | 98 | 90 | 6 |
| 15 | — | 84 | 88 | 81 | 96 | 87 | 7 |
| 20 | 76 | 85 | 86 | 75 | 97 | 84 | 9 |
| 25 | — | 85 | 81 | 82 | 96 | 86 | 7 |
| 30 | — | 83 | 83 | 76 | 94 | 84 | 7 |
| 40 | — | 80 | 82 | 82 | 92 | 84 | 5 |
| 50 | — | 78 | 79 | 79 | 98 | 84 | 10 |
| 60 | — | 74 | 73 | 80 | 97 | 81 | 11 |
| 120 | — | 68 | 86 | 82 | 102 | 84 | 13 |
| 180 | — | 71 | 93 | 88 | 99 | 88 | 12 |
| 360 | — | 59 | 83 | 51 | 94 | 72 | 20 |
| 1440 | 66 | 50 | 65 | 88 | 98 | 73 | 19 |

Concluding Remarks

The foregoing description details specific methods which can be employed to practice the present invention. Having detailed such specific methods, those skilled in the art will well enough know how to devise alternative reliable methods at arriving at the same information in using the fruits of the present invention. Thus, however detailed the foregoing may appear in text, it should not be construed as limiting the overall scope thereof; rather, the ambit of the present invention is to be determined only by the lawful construction of the appended claims. All documents cited herein are hereby expressly incorporated by reference herein.

What is claimed is:

1. A method of delivering functional biological materials to a localized region of a lung, said method comprising:
   providing a delivery device, said device having at least an expulsion system and an end distal to said expulsion system, and positioning said delivery device such that said distal end is adjacent to said localized region of the lung; and introducing said materials within a solution or suspension through said delivery device, wherein said material is deposited only on a limited surface area of the lung adjacent to said distal end of said delivery device.

2. The method of claim 1, wherein said delivery device deliver said material in discrete droplets having a diameter greater than about 20 $\mu$m an 1 less than about 500 $\mu$m.

3. The method according to claim 2 where n the discrete droplets have a volume median diameter ranging from 130 $\mu$m to 225 $\mu$m.

4. The method according to claim 3 or 2 in which the discrete droplets are propelled at a velocity of approximately 0.2 to 100 m/sec.

5. The method of claim 4, wherein said velocity is approximately 1 m/sec to about 50 m/sec.

6. The method according to claim 2 wherein the functional biological materials are selected from a group consisting of viral vectors growth factors, cytokines, anti-inflammatories, anti-cancer agents, antivirals, antibiotics, immunosuppressants, immunostimulants, anesthetics, mucolytics or viscolytics.

7. The method according to claim 6 wherein the discrete droplets have a volume median diameter ranging from 130 $\mu$m to 225 $\mu$m.

8. The method according to claim 6 wherein the discrete droplets are propelled at a velocity of approximately 0.2 m/sec. to 100 m/sec.

9. A method according to claim 2 wherein said discrete droplets have a volume median diameter of about 150 $\mu$m.

10. A method according to claim 2 wherein said discrete droplets have a volume median diameter of about 180 $\mu$m.

11. A method according to claim 2 wherein said discrete droplets have a volume median diameter of about 190 $\mu$m.

12. A method according to claim 2 wherein said discrete droplets have a volume median diameter of about 200 $\mu$m.

13. A method according to claim 1 wherein the biologic material is a viral vector.

14. A method according to claim 13 wherein said viral vector comprises and adenoviral vector.

15. A method according to claim 14 wherein said adenoviral vector comprises a cystic fibrosis transmembrane conductance regulator gene.

16. A method according to claim 1 wherein the biologic material is a mucolytic.

17. A method according to claim 1 wherein the biologic material is a viscolytic.

18. A method according to claim 1 wherein said biologic material is recombinant human deoxyribonuclease.

19. The method according to claim 1 wherein the solution or suspension is provided by a vehicle selected from water or glycerol.

20. The method according to claim 1 wherein the solution or suspension volume delivered ranges from about 10 $\mu$L to about 2,000 $\mu$l.

21. The method according to claim 1 wherein the functional biological materials are selected from a group consisting of viral vectors, growth factors, cytokines, anti-inflammatories, anti-cancer agents, antivirals, antibiotics, immunosuppressants, immunostimulants, anesthetics, mucolytics or viscolytics.

22. The method of claim 1 wherein said delivery device comprises a nozzle at said distal end.

23. The method of claim 1, wherein said localized region is substantially at or before a first or second bifurcation in the lung located downstream, in relation to the flow of materials delivered, from the position of said distal end of said delivery device.

24. The method of claim 1, wherein said localized region is limited to the lung's upper airway passages.

25. The method of claim 1, wherein said localized region excludes the lung's.

* * * * *